United States Patent [19]

Böckmann et al.

[11] 4,276,231

[45] Jun. 30, 1981

[54] PROCESS FOR THE PREPARATION OF OPTIONALLY SUBSTITUTED BENZOYL CHLORIDE

[75] Inventors: Walter Böckmann; Karl-August Lipper; Friedrich Brühne, all of Krefeld, Fed. Rep. of Germany

[73] Assignee: Bayer Aktiengesellschaft, Leverkusen, Fed. Rep. of Germany

[21] Appl. No.: 71,805

[22] Filed: Sep. 4, 1979

[30] Foreign Application Priority Data

Sep. 23, 1978 [DE] Fed. Rep. of Germany ....... 2841541

[51] Int. Cl.³ ...................... C07C 51/60; C07C 51/58
[52] U.S. Cl. ........................... 260/544 D; 210/544 L; 210/544 N; 423/488; 423/240
[58] Field of Search .......... 260/544 D, 544 N, 544 L; 423/488, 240

[56] References Cited

U.S. PATENT DOCUMENTS

| | | | |
|---|---|---|---|
| 1,557,154 | 10/1925 | George | 260/544 D |
| 2,558,011 | 6/1951 | Sprauer et al. | 423/488 |
| 3,260,059 | 7/1966 | Rosenberg et al. | 423/488 |
| 3,537,818 | 11/1970 | Jubin et al. | 423/488 |
| 3,691,217 | 9/1972 | McCann | 260/544 D |
| 3,835,187 | 9/1974 | Dyson | 260/544 D |
| 4,091,017 | 8/1978 | Richtzenhain et al. | 260/544 D |

FOREIGN PATENT DOCUMENTS

| | | | |
|---|---|---|---|
| 609682 | 11/1960 | Canada | 423/488 |
| 11494 | 10/1980 | Fed. Rep. of Germany | 260/544 D |
| 293924 | 7/1928 | United Kingdom | 260/544 D |
| 395320 | 1/1974 | U.S.S.R. | 423/488 |

*Primary Examiner*—Howard T. Mars
*Attorney, Agent, or Firm*—Sprung, Felfe, Horn, Lynch & Kramer

[57] ABSTRACT

A process for the preparation of optionally substituted benzoyl chloride from optionally substituted benzotrichloride at elevated temperature in the presence of a catalyst is described wherein optionally substituted benzotrichloride or a mixture thereof with optionally substituted benzoyl chloride is reacted with an excess of 1 to 20 mol percent of optionally substituted benzoic acid and/or water and the hydrogen chloride-containing off-gases formed during the reaction are washed with optionally substituted benzotrichloride or the mixture of optionally substituted benzotrichloride and optionally substituted benzoyl chloride.

22 Claims, No Drawings

PROCESS FOR THE PREPARATION OF OPTIONALLY SUBSTITUTED BENZOYL CHLORIDE

The invention relates to a process for the preparation of optionally substituted benzoyl chloride by reacting optionally substituted benzotrichloride or a mixture of optionally substituted benzotrichloride and optionally substituted benzoyl chloride, with optionally substituted benzoic acid and/or water in the presence of catalysts.

It is known to prepare benzoyl chloride by reacting equimolar amounts of benzotrichloride and benzoic acid in the presence of zinc chloride (German Patent Specification No. 11,494).

It is also known to prepare benzoyl chloride by reacting equimolar amounts of benzotrichloride with water in the presence of iron chloride (German Patent Specification No. 331,696).

A further process for the preparation of benzoyl chloride is known from U.S. Pat. No. 1,557,154. According to this process, benzotrichloride is reacted with water at elevated temperature in the presence of a suspended catalyst, and the amount of water added should not be substantially more than 110% of the amount of water theoretically required for the reaction.

A process for the preparation of optionally substituted benzoyl chloride from optionally substituted benzotrichloride at elevated temperature in the presence of catalysts has been found, which is characterized in that the optionally substituted benzotrichloride, or a mixture of the optionally substituted benzotrichloride and the optionally substituted benzoyl chloride, is reacted with an excess of about 1 to about 20 mol % (based on the optionally substituted benzotrichloride employed) of optionally substituted benzoic acid and/or water, the hydrogen chloride-containing off-gases formed during the reaction being washed with the optionally substituted benzotrichloride employed or the mixture of optionally substituted benzotrichloride and optionally substituted benzoyl chloride employed.

The optionally substituted benzotrichloride employed in the process according to the invention can be a benzotrichloride which corresponds to the general formula

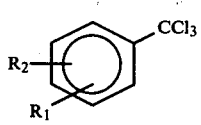

wherein $R_1$ and $R_2$ can be identical or different and represent hydrogen, halogen or nitro or alkyl groups.

The optionally substituted benzoic acid employed can be a benzoic acid which corresponds to the general formula

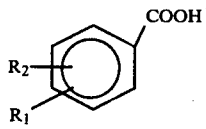

wherein $R_1$ and $R_2$ have the meaning indicated above.

Suitable radicals $R_1$ and $R_2$ are, for example, hydrocarbons with up to 6 C atoms, for example alkyl radicals, such as methyl, ethyl, n-propyl, isopropyl, n-butyl, isobutyl, tert.-butyl, n-pentyl, isopentyl, 2-methylpentyl, 3-methylpentyl, n-hexyl and isohexyl and also cyclohexyl.

Halogens which may be mentioned are fluorine, chlorine and bromine, preferably chlorine.

Benzotrichloride and o-chloro- or p-chloro-benzotrichloride are preferably reacted according to the process of the invention.

The process according to the invention is generally carried out in the presence of acid catalysts.

For example, the following acid catalysts may be mentioned: $HClO_4$, $H_2SO_4$, $H_2S_2O_7$, $H_3PO_4$, $H_4P_2O_7$, aromatic or aliphatic sulphonic acids with up to 15 C atoms, such as p-toluenesulphonic acid, nonafluorobutanesulphonic acid and naphthalenesulphonic acid, and also halides of the elements boron, aluminium, gallium, germanium, tin, arsenic, antimony, bismuth, copper, zinc, cadmium, titanium, zirconium, vanadium, niobium, chromium, molybdenum, tungsten, iron, cobalt and nickel.

Preferably, $H_2SO_4$, $H_3PO_4$, $FeCl_2$, $ZnCl_2$ and/or $FeCl_3$ are employed in the process according to the invention.

According to the process of the invention it is contemplated that the metal chlorides used not be employed as such direct in the process but be used in the form of the corresponding oxides, hydroxides and/or carbonates, which then form the corresponding metal chlorides with the hydrogen chloride which forms during the reaction.

In addition to the oxides, hydroxides and/or carbonates, one can employ metal salts of other acids, such as of sulphuric acid, phosphoric acid, acetic acid or oleic acid and also of naphthenic acid, or the metals themselves, in the process according to the invention.

In general, the catalysts, which can be employed on their own or as a mixture with one another, are used in an amount of about 0.005 to 10% by weight and preferably in an amount of 0.02 to 3% by weight, based on the benzoyl chloride formed.

In a preferred embodiment of the process according to the invention, the catalyst is employed in the form of an aqueous solution. In this case, the amount of catalyst in the solvent is about 0.2 to 98% by weight and preferably 0.5 to 30% by weight.

According to the process of the invention, the optionally substituted benzotrichloride, or the mixture of the optionally substituted benzotrichloride and the optionally substituted benzoyl chloride, is reacted with an excess of about 1 to 20 mol % (based on the optionally substituted benzotrichloride employed), and preferably with an excess of 3 to 8 mol %, of optionally substituted benzoic acid and/or water.

If the reaction is carried out with optionally substituted benzoic acid and water at the same time, the weight ratio of optionally substituted benzoic acid to water can assume any conceivable value without this resulting in an adverse influence on the reaction.

The composition of the mixture of optionally substituted benzotrichloride and optionally substituted benzoyl chloride employed in the process according to the invention can vary within wide limits. Preferably, mixtures of about 5 to 99%, and preferably 20 to 99%, of optionally substituted benzotrichloride and about 1 to 95%, and preferably 1 to 80%, of optionally substituted benzoyl chloride are employed.

The reaction is customarily carried out at temperatures in the range of about 70° to 200° C. and preferably of 120° to 160° C.

The reaction can be carried out under normal pressure, under reduced pressure or under elevated pressure; the reaction preferably takes place under normal pressure. Pressures from 0.8 bar up to 2 bar, preferably from 0.9 bar to 1.2 bar, are contemplated.

According to the invention, the hydrogen chloride-containing off-gases which are evolved during the reaction are washed with the optionally substituted benzotrichloride, or the mixture of optionally substituted benzotrichloride and optionally substituted benzoyl chloride, which is to be employed.

In addition, the hydrogen chloride-containing off-gases can also be washed with circulated reaction product and/or with inert aliphatic, cycloaliphatic and/or aromatic hydrocarbons with up to 15 C atoms and preferably up to 10 C atoms, which are optionally substituted by halogens, such as fluorine, chlorine or bromine, preferably by chlorine.

Examples which may be mentioned of optionally substituted aliphatic hydrocarbons are: carbon tetrachloride, trichloroethylene and hexane; of optionally substituted cycloaliphatic hydrocarbons are: cyclohexane, methylcyclohexane and decalin; and of optionally substituted aromatic hydrocarbons are: benzene, chlorobenzene, toluene, xylene and chlorotoluene.

Preferably, toluene, xylene and chlorotoluene are employed for washing the HCl-containing off-gases.

According to a preferred embodiment of the process according to the invention, washing of the hydrogen chloride-containing off-gases is carried out as follows:

The HCl-containing off-gases which issue from the reactor or reactors are washed in a wash tower in counter-current with the liquid, hot reaction mixture from the first reactor.

The off-gas is then fed to a second wash tower where it is washed at room temperature with the optionally substituted benzotrichloride or the mixture of optionally substituted benzotrichloride and optionally substituted benzoyl chloride in counter-current.

The off-gas then passes into a third wash tower, where it is washed at low temperatures with inert, optionally substituted aromatic and/or aliphatic solvents. Toluene is preferably employed as the inert solvent.

By means of the wash according to the invention, a hydrogen chloride-containing off-gas is obtained which is virtually free from organic constituents, such as optionally substituted benzoyl chloride, optionally substituted benzotrichloride or optionally substituted benzoic acid, and is suitable, for example, for hydrogen chloride electrolysis, or can be condensed, by adiabatic absorption, to very pure aqueous hydrochloric acid.

In addition, losses of reactants which are still present in the off-gas are avoided by washing the hydrogen chloride-containing off-gas.

In a preferred embodiment of the process according to the invention, the bottom product which remains after distillation of the reaction product and consists of about 20 to 70% by weight of optionally substituted benzoyl chloride, 20 to 70% by weight of optionally substituted benzoic acid and 0.05 to 10% by weight of catalyst is reacted with a molar excess of optionally substituted benzotrichloride. The molar excess of optionally substituted benzotrichloride is generally 3 to 150% and preferably 10 to 100%, based on the amount of optionally substituted benzoic acid present in the bottom product.

The reaction of the bottom product with the optionally substituted benzotrichloride is generally carried out at temperatures in the range of about 70° to 200° C. and preferably at 120° to 160° C.

The hydrogen chloride-containing off-gases evolved during this reaction can, as described above, be washed with the optionally substituted benzotrichloride to be employed, or with the mixture of optionally substituted benzotrichloride and optionally substituted benzotrichloride. The hydrogen chloride-containing off-gas can additionally be washed with circulated reaction product and/or with the inert, optionally substituted aliphatic, cycloaliphatic and/or aromatic hydrocarbons mentioned above.

When the bottom product is reacted with optionally substituted benzotrichloride it is generally no longer necessary to add a catalyst, since catalyst is still present in the bottom product. If necessary, however, the catalysts described above can be added, the amount of catalyst being about 0.005 to 10% by weight and preferably 0.02 to 3% by weight, based on the benzoyl chloride formed.

After reaction of the bottom product with the optionally substituted benzotrichloride, the resulting reaction mixture is distilled and a mixture of optionally substituted benzotrichloride and optionally substituted benzoyl chloride is obtained and this is recycled as feed product into the main reaction.

The process according to the invention can be carried out either discontinuously or continuously.

In the continuous procedure, the reaction of the optionally substituted benzotrichloride, or of the mixture of optionally substituted benzotrichloride and optionally substituted benzoyl chloride, with optionally substituted benzoic acid and/or water is preferably carried out in several reactors connected to one another, particularly preferentially in 2 to 5 reactors.

In this procedure, for example, in order to prepare benzoyl chloride, benzotrichloride or the mixture of benzotrichloride and benzoyl chloride, together with benzoic acid and/or water and the catalyst, is metered continuously into the first reactor. The reaction mixture then flows continuously into the other reaction vessels (if several are present), where the reaction goes to completion, and finally passes into a distillation unit. In this unit, the reaction mixture is distilled continuously, preferably in vacuo, under about 12 to 190 mbars, and at temperatures in the range of about 70° to 140° C. and a pure, benzotrichloride-free, benzoyl chloride is obtained. The bottom product from the distillation is reacted at about 70° to 200° C., preferably at 120° to 160° C., with an approximately 3 to 150% molar excess of benzotrichloride, based on the amount of benzoic acid present in the bottom product, and the mixture of benzotrichloride and benzoyl chloride obtained therefrom after the distillation is recycled as feed product into the main reaction, where fresh benzotrichloride is added thereto, for a further reaction.

The reaction of the bottom product can be carried out either discontinuously or continuously. In the continuous procedure, the reaction is usually carried out in several reactors connected downstream of one another, preferably in 2 to 5 reactors.

As described above, the hydrogen chloride-containing off-gas formed during the reaction is washed with the optionally substituted benzotrichloride or a mixture of optionally substituted benzotrichloride and optionally substituted benzoyl chloride and optionally is additionally washed with circulated reaction product and-/or inert organic solvents.

According to the process of the invention, the optionally substituted benzoyl chloride is obtained in a yield of 96-98% of theory and in a purity of more than 99.5%.

Compared with the prior art, the process according to the invention has the following advantages:

The use of an excess of optionally substituted benzoic acid and/or water ensures that the conversion of the optionally substituted benzotrichloride proceeds to completion and that the optionally substituted benzoyl chloride formed is always free from the corresponding benzotrichloride. This measure results in a saving in distillation costs, since the distillation to obtain a pure product is less expensive. Specifically, a benzoyl chloride which is absolutely free from benzotrichloride is required for many fields of application and this can be provided in a simple manner by this procedure.

Furthermore, optionally substituted benzoic acid and water can be employed for the reaction at the same time in the same installation without changing the process conditions, without a restriction of the molar ratio of optionally substituted benzoic acid to water being required. This variable procedure makes it possible to adapt in the short term to the prevailing conditions in practice, such as the availability of raw materials, for example benzoic acid, or the sales possibilities for hydrogen chloride or aqueous hydrochloric acid.

Additionally, the effect of the various measures for washing the hydrogen chloride formed is that no other reactants are lost with the stream of off-gas and the stoichiometry of the reaction is thus always easy to maintain and that, after washing, the HCl gas produced is virtually free from organic impurities and can be employed direct for hydrochloric acid electrolysis or can be converted by absorption in water to very pure aqueous hydrochloric acid, which is suitable for virtually all fields of application.

A further effect of washing is that the off-gas lines no longer become blocked by solids and thus disturb the operation cycle.

Moreover, pollution of the environment is particularly low with the process according to the invention, since no contaminated effluents or off-gases are produced. The resulting highly pure hydrogen chloride can be converted to chlorine gas and thus recycled, via the preparation of the benzotrichlorides, into the process again. The economy of the preparation of benzoyl chloride is considerably increased by the measures described.

The optionally substituted benzoyl chloride prepared by the process according to the invention is a valuable intermediate product for the preparation of optionally substituted benzoyl peroxide, benzophenone, benzyl benzoate, benzoylcellulose and benzamide and of dyestuffs and medicaments (compare Ullmann's Enzyklopädie der technischen Chemie (Ullmann's Encyclopaedia of Industrial Chemistry), 4th edition, Volume 8, page 372-373, Verlag Chemie, Weinheim 1974 and Kirk-Othmer, Encyclopedia of Chemical Technology, 2nd edition, Volume 3, page 430-431, Interscience Publishers, New York, London, Sydney 1964).

EXAMPLE 1

13.6 g of anhydrous zinc chloride are added to 1,832 g (15.0 mols) of benzoic acid in a 5 l flask fitted with a stirrer, a reflux condenser, a thermometer and a dropping funnel and the mixture is heated to 140° C. and kept at this temperature. 2,737 g (14.0 mols) of benzotrichloride are now added dropwise in the course of 2 hours, whilst stirring, and the reaction product is then kept at 140° C. for a further 2 hours. The HCl off-gas which issues from the reflux condenser is washed in a wash tower packed with Raschig rings with 2,737 g of benzotrichloride, which is circulated by means of a pump, and is then condensed to give approximately 30% strength aqueous hydrochloric acid. This hydrochloric acid contains 18 ppm of organically bonded carbon. The benzotrichloride used for washing the HCl can be employed again as the starting material for the next experiment. According to distillation analysis, the content of benzoic acid and benzoic anhydride in the crude benzoyl chloride is 3.5% by weight. Distillation under a pressure of 50 mbars gives 3,805 g (=96.7% of theory) of pure, benzotrichloride-free benzoyl chloride.

In a comparison experiment without washing of the HCl off-gas, the 30% strength hydrochloric acid formed contains 124 ppm of organically bonded carbon.

EXAMPLE 2

4,887 g (25.0 mols) of benzotrichloride are heated to 150° C. in a 5 l flask fitted with a stirrer, a reflux condenser and a dropping funnel. 483 g of 3% strength aqueous sulphuric acid are then allowed to run in at this temperature, in the course of 5 hours. After the addition of sulphuric acid is complete, the reaction product is stirred for a further 2 hours at 150° C. According to distillation analysis, the content of benzoic acid and benzoic anhydride in the crude benzoyl chloride is 3.8% by weight. Distillation of the reaction product in vacuo under 50 mbars gives 3,255 g (92.6% of theory) of pure, benzotrichloride-free benzoyl chloride and 210 g of a distillation bottom product. The latter is heated with 260 g (1.3 mols) of benzotrichloride to 150° C. in a stirred vessel fitted with a reflux condenser and the mixture is kept at this temperature for 2 hours. Distillation under 50 mbars gives 368 g of a mixture of benzotrichloride and benzoyl chloride which has a benzotrichloride content of 13.0% by weight. This product can be employed again as starting material for the next batch. When the mixture of benzotrichloride and benzoyl chloride which is recovered is taken into account, the yield of pure benzoyl chloride increases to 97.3% of theory.

The HCl off-gas which issues during the main reaction and during working up of the distillation bottom product is washed in a wash tower packed with Raschig rings with 4,887 g of benzotrichloride, which is circulated by means of a pump, and is then condensed to give an approximately 25% strength aqueous hydrochloric acid. The hydrochloric acid contains 22 ppm of organically bonded carbon. Like the mixture of benzotrichloride and benzoyl chloride which is recovered, the benzotrichloride used for washing the off-gas is employed again as starting material for the next batch.

EXAMPLE 3

830 g/hour of benzotrichloride, 345 g/hour of a mixture of benzotrichloride and benzoyl chloride (22.6% by weight of benzotrichloride), 403 g/hour of liquid benzoic acid and 37 g/hour of a 2.5% strength solution of iron(II) chloride in water are introduced by means of metering pumps into the first vessel of a cascade of four reaction vessels, each of which has a useful volume of 2.5 l. The mixture of benzotrichloride and benzoyl chloride is obtained when working up the bottom product from the benzoyl chloride distillation, as will be described further below. The reaction product from the first vessel runs off freely through a side outlet into the second vessel, from where it runs off into the third vessel and then into the fourth vessel. The contents of the four reaction vessels are stirred and kept at a temperature of 150° C.

The product which runs off from the fourth reaction vessel passes via a cooler into an intermediate vessel. After an operating time of 24 hours, a stationary state of equilibrium has been reached in the four reaction vessels. Analysis, by gas chromatography, of the crude benzoyl chloride which runs off from the fourth vessel shows that no further benzotrichloride is present. According to distillation analysis, the crude product contains 6.0% by weight of benzoic acid and benzoic anhydride. Continuous distillation of the crude product under 50 mbars gives, per hour, 1,198 g of pure, benzotrichloride-free benzoyl chloride and 172 g of distillation bottom product.

The amount of distillation bottom product obtained in 12 hours (2,064 g) is heated with 2,718 g of benzotrichloride to 150° C. in a stirred vessel fitted with a reflux condenser and the mixture is kept at this temperature for 2 hours. Distillation under 50 mbars gives 4,140 g of a mixture of benzotrichloride and benzoyl chloride with a benzotrichloride content of 22.6% by weight of this mixture is metered back into the first vessel of the four-stage cascade.

The HCl off-gas which issues from the four reaction vessels of the cascade and from the reaction vessel for the reaction of the bottom product from the benzoyl chloride distillation with benzotrichloride is combined and washed, firstly in a wash tower with the circulated reaction product from the first reaction vessel and then, in a second wash tower, with the benzotrichloride employed for the main reaction and the mixture of benzotrichloride and benzoyl chloride. After a further wash in a third wash tower with toluene, which is at a temperature of −25° C., the HCl off-gas is condensed to give approximately 30% strength hydrochloric acid. This hydrochloric acid contains a maximum of 5 ppm of organically bonded carbon.

The total yield of benzoyl chloride, based on the benzoic acid and benzotrichloride employed, is 97.9% of theory.

EXAMPLE 4

4,599 g (20.0 mols) of p-chloro-benzotrichloride are heated to 150° C. in a 5 l flask fitted with a stirrer, a reflux condenser and a dropping funnel. A solution of 2.4 g of iron(II) sulphate in 378 g of water is then allowed to run in at this temperature, in the course of 4 hours. The reaction product is then stirred at 150° C. for a further 2 hours. Distillation in vacuo under 70 mbars gives 3,213 g (91.8% of theory) of pure, p-chloro-benzotrichloride-free p-chloro-benzoyl chloride and 226 g of distillation bottom product. The latter is heated with 286 g (1.24 mols) of p-chloro-benzotrichloride to 150° C. in a stirred vessel fitted with a reflux condenser and the mixture is kept at this temperature for 2 hours. Distillation in vacuo under 70 mbars gives 410 g of a mixture of p-chloro-benzotrichloride and p-chloro-benzoyl chloride with a p-chloro-benzotrichloride content of 8.8% by weight. This product can be employed again as starting material for the next batch. When the mixture of p-chloro-benzotrichloride and p-chloro-benzoyl chloride which is recovered is taken into account, the yield of pure p-chloro-benzoyl chloride increases to 96.9% of theory.

The HCl gas which issues during the main reaction and during working up of the distillation bottom product is washed in a wash tower packed with Raschig rings with 4,599 g of p-chloro-benzotrichloride, which is circulated by means of a pump, and is then condensed to give an approximately 26% strength aqueous hydrochloric acid. The hydrochloric acid contains 18 ppm of organically bonded carbon. Like the mixture of p-chloro-benzotrichloride and p-chlorobenzoyl chloride which is recovered, the p-chloro-benzotrichloride used for washing the off-gas is employed again as starting material for the next batch.

What is claimed is:

1. In a process for the preparation of optionally substituted benzoyl chloride from optionally substituted benzotrichloride which process is performed at elevated temperature in the presence of a catalyst the improvement consisting essentially of reacting an optionally substituted benzotrichloride having the general formula

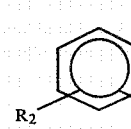

wherein $R_1$ and $R_2$ are identical or different and represent hydrogen, halogen, nitro or alkyl,
or a mixture of said optionally substituted benzotrichloride and optionally substituted benzoyl chloride with a 1 to 20 mol percent excess, based on said optionally substituted benzotrichloride employed, of optionally substituted benzoic acid of the general formula

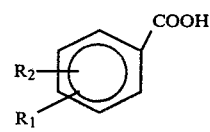

wherein $R_1$ and $R_2$ can be identical or different and represent hydrogen, halogen, nitro or alkyl,
and/or liquid water, the hydrogen chloride containing off-gases formed during the reaction being washed with the optionally substituted benzotrichloride employed or the mixture of optionally substituted benzotrichloride and optionally substituted benzoyl chloride employed and/or with an inert, optionally substituted aliphatic, cycloaliphatic, and/or aromatic hydrocarbon having up to 15 carbon atoms, the reaction mixture being subjected to distillation and the bottom product which remains after distillation of optionally substituted benzoyl chloride being reacted with a 3 to 150% molar excess of optionally substituted benzotrichloride, based on the amount of optionally substituted benzoic acid present in the bottom product, and the mixture of optionally substituted benzotrichloride and optionally substituted benzoyl chloride which is obtained therefrom after distillation being recycled as feed product into the main reaction.

2. A process according to claim 1 wherein benzotrichloride or ortho-chloro-or para-chloro-benzotrichloride is employed.

3. A process according to claim 1 wherein the hydrogen chloride-containing off-gas evolved during the reaction is washed with the circulated reaction product, that is, the mixture of optionally substituted benzotrichloride and optionally substituted benzoyl chloride, and/or with inert, optionally substituted aliphatic, cycloaliphatic, and/or aromatic hydrocarbons having up to 15 carbons atoms.

4. A process according to claim 3 wherein the hydrogen chloride-containing off-gas is washed with toluene, chlorotoluene and/or xylene.

5. A process according to claim 1 wherein the optionally substituted benzotrichloride or the mixture of optionally substituted benzotrichloride and optionally substituted benzoyl chloride is reacted with a benzoic acid.

6. A process according to claim 1 wherein the optionally substituted benzotrichloride or the mixture of optionally substituted benzotrichloride and optionally substituted benzoyl chloride is reacted with water.

7. A process according to claim 1 wherein the optionally substituted benzotrichloride or the mixture of optionally substituted benzotrichloride and optionally substituted benzoyl chloride is reacted with a mixture of benzoic acid and water.

8. A process according to claim 1 wherein the reaction of benzotrichloride with water or optionally substituted benzoic acid is carried out in the presence of zinc chloride.

9. A process according to claim 1 wherein the reaction of said benzotrichloride with water or optionally substituted benzoic acid is carried out in the presence of aqueous sulfuric acid.

10. A process according to claim 1 wherein the reaction of said optionally substituted benzotrichloride with water or optionally substituted benzoic acid is carried out in the presence of iron(II) chloride.

11. A process according to claim 1 wherein the reaction of said optionally substituted benzotrichloride with water or said optionally substituted benzoic acid is carried out in the presence of iron(II) sulfate.

12. A process according to claim 6 wherein the hydrogen chloride-containing off-gases are washed with an optionally substituted hydrocarbon having up to 10 carbon atoms.

13. A process according to claim 5 wherein said hydrogen chloride-containing off-gases are washed with optionally substituted hydrocarbons having up to 10 carbon atoms.

14. A process according to claim 5 wherein said hydrogen chloride-containing off-gases are washed with optionally substituted benzotrichloride.

15. A process according to claim 6 wherein said hydrogen chloride-containing off-gases are washed with optionally substituted benzotrichloride.

16. A process according to claim 5 wherein said hydrogen chloride-containing off-gases are washed with optionally substituted benzoyl chloride.

17. A process according to claim 6 wherein said hydrogen chloride-containing off-gases are washed with optionally substituted benzoyl chloride.

18. A process according to claim 6 wherein the reaction of said optionally substituted benzotrichloride with water is carried out in the presence of zinc chloride.

19. A process according to claim 6 wherein the reaction of said optionally substituted benzotrichloride with water is carried out in the presence of aqueous sulfuric acid.

20. A process according to claim 6 wherein the reaction of said optionally substituted benzotrichloride with water is carried out in the presence of iron(II) chloride.

21. A process according to claim 6 wherein the reaction of said optionally substituted benzotrichloride with water is carried out in the presence of iron(II) sulfate.

22. A process according to claim 6 wherein the hydrogen chloride-containing off-gas is washed with a hydrocarbon of up to 10 carbon atoms.

* * * * *